United States Patent [19]

Kita et al.

[11] Patent Number: 5,252,557
[45] Date of Patent: Oct. 12, 1993

[54] ADMINISTRATION METHOD OF ANTITHROMBIN

[75] Inventors: Kiyoshi Kita, Tokyo; Fumiaki Yoshitomi, Fukuoka, both of Japan

[73] Assignee: Kiyoshi Kita, Tokyo, Japan

[21] Appl. No.: 636,710

[22] Filed: Jan. 2, 1991

Related U.S. Application Data

[63] Continuation-in-part of Ser. No. 391,323, Jul. 25, 1989, Pat. No. 5,182,259.

[30] Foreign Application Priority Data

Jan. 19, 1990 [JP] Japan ..................... 2-8230

[51] Int. Cl.$^5$ ............... A61K 37/02; A61K 31/735; A61F 2/30; C07K 15/14
[52] U.S. Cl. ..................... 514/8; 514/54; 514/57; 530/393; 424/530; 604/890.1; 604/49; 623/18
[58] Field of Search ............. 514/8, 54, 57; 604/890.1, 49; 623/18; 530/393; 424/530

[56] References Cited

U.S. PATENT DOCUMENTS

| | | | |
|---|---|---|---|
| 4,141,973 | 2/1979 | Balazs | 424/180 |
| 4,340,589 | 7/1982 | Uemura et al. | 530/393 |
| 4,623,718 | 11/1986 | Collen | 530/393 |
| 4,690,973 | 9/1987 | Noishiki et al. | 530/356 |
| 4,889,722 | 12/1989 | Sheffield et al. | 424/450 |
| 4,971,955 | 11/1990 | Soll et al. | 514/54 |
| 4,983,585 | 1/1991 | Pennell et al. | 514/57 |

OTHER PUBLICATIONS

Nishimura et al., Chem. Abstracts, vol. 99:11067/w (1983).
A. Ferbert et al., BWtPA Acute Embolic Apoplexy Investigation Group, U.S.A. and Germany, Medical Tribune, Japan, 1989, The 1st. International Apoplexy Congress.
U. Abildgaard, Antithrombin Deficiency, KabiVitrum AB, Sweden, 1988.
Antithrombin, Kabi Plasma Products, Sweden, 1989.
K. Horie, Fragrance Journal, No. 9, pp. 160–166, 1988, Japan.
E. F. Mammen et al., Biologia & Clinica Hematologica, 9, Supl. 1, 69–73, 1987.
Medical Tribune, Japan, 1989, The 1st. International Apoplexy Congress.
Z. Darzynkiewicz and E. A. Balazs, Effect of Connective Tissue Intercellular Matrix on Lymphocyte Stimulation. (1971) pp. 113–123, Exper. Cell Res.

*Primary Examiner*—Jacqueline Stone
*Attorney, Agent, or Firm*—Staas & Halsey

[57] ABSTRACT

An antithrombin solution for preventing fibrin formations, including antithrombin at a concentration of more than 0.5 U/ml and not more than 250 U/ml, a physiological buffer and optionally sodium hyaluronate. A related surgical method includes applying the solution directly during surgery to exposed tissue. The solution can also be injected into the synovial cavity of patients with active arthritis as therapeutic orthopaedics.

9 Claims, No Drawings

ADMINISTRATION METHOD OF ANTITHROMBIN

This application is a continuation-in-part application of copending U.S. Ser. No. 391,323, filed Jul. 25, 1989 and entitled INTRAOCULAR ANTICOAGULANT COMPRISING ANTITHROMBIN III AND METHOD OF MANUFACTURE, now U.S. Pat. No. 5,182,259.

BACKGROUND OF THE INVENTION

Most of the joints in the body represent synovial joints which have four distinguishing features: (1) the articulating surfaces of the bones are covered with hyaline cartilage called articulating cartilage; (2) the joint is enclosed by an articular capsule or joint capsule; (3) the inner layer of the joint capsule is lined with a thin vascular synovial membrane; and (4) the synovial membrane encloses a cavity into which a synovial fluid is secreted.

The causes of arthritis include trauma to a joint, bacterial infection and metabolic disorders.

Rheumatoid arthritis, the most important clinically, begins with inflammation of the synovial membrane; the inflammed synovial membrane produces an abnormal tissue known as pannus which grows over the articular cartilage. The articular cartilage is distorted and is occasionally destroyed. Current medications for arthritis include sodium aurothiomalate, penicillamine, antipyretic antiphlogistics such as aspirin and indomethacin, and corticosteroids. The severe pain caused by active arthritis can be temporarily relieved through the administration of hydrocortisone which shows a strong anti-inflammatory effect and also makes hyaluronic acid (hereinafter referred to as HA) in normal highly polymerized states. Corticosteroids are prescribed, even though, it is common knowledge for doctors to be cautious of the side effects like osteoporosis from a long-term prescription of corticosteroids.

The volume of abnormal HA in the synovial fluid increases in cases of infectious and rheumatoid arthritis. This abnormal HA is not properly polymerized and therefore can not maintain or improve joint function. If a properly polymerized HA could be introduced into the joint capsule, the treatment would be much more effective. From that point of view, a local injection of HA has recently been made available as an injection into the synovial cavity of osteoarthritis.

In the wound healing process following surgical operations beginning with the dissection of the skin, ineffective adhesion due to scars on each surgically traumatized organ may result and cause pain, mechanical ileus, functional disturbance, motor disturbance or orthopaedic impairment at the surgical region. These complications occur with the following steps: (1) surgical trauma to the organs; (2) inflammatory exudates, especially fibrin, are secreted on those tissues; (3) fibrino-fibrous inflammation on the tissues; (4) the fibrous strands on the organ contract; and (5) the complications occur.

Balazs et al. in *Biology of the Fibroplast*, pp. 237-252, Academic Press, London, 1973, reported in 1973 that HA inhibits cell migration and multiplication of certain cells in vitro. And it is speculated that HA influences the invasion and activity of cells participating in the acute and chronic inflammatory process and it is though to prevent fibrous tissue formation. However, it does not effectively suppress the formation of fibrin which is converted from excessive fibrinogen under a hypercoagulated condition.

At the same time, there are some reports that HA has a procoagulant activity. If this is true, the fibrin clot formation is to be promoted in areas having fibrinous inflammation like arthritis which may result in more severe ankylosis. Biological activities of implanted HA in the body are not well defined presently. It has not been proven that HA has an anti-inflammatory effect in biological inflammatory processes. It may cease the inflammation of osteoarthritis by improving the cushion effect and mechanical separation of tissues in the joint, not by relating to theoretical inflammation processes directly.

Even if HA indirectly effects the inflammation process, it does not effectively inhibit fibrous tissue formation, pannus nor ankylosis.

Implanted HA in the joint would temporarily be a physical barrier, not a biological inhibitor, for the invasion of exudates such as fibrin and inflammatory cells. Even though, it is considered that the implanted HA would mix with various inflammatory exudates under the mobility of the joint, and would be unable to inhibit the cell migration and fibrin clot formation in the synovial cavity.

LeBoeuf et al. in the "Journal of Biological Chemistry", Vol. 261, No. 27, pp. 12586-12592, 1986,"; reported in 1986 that human fibrinogen specifically binds hyaluronic acid in vitro, and suggested a close interaction between fibrin and HA. Moreover, excessive fibrinogen is more quickly converted to fibrin under the conditions of a depressed activity of plasminogen activator or lowered antithrombin concentrations which occur within the inflammed area.

SUMMARY OF THE INVENTION

The formation of the fibrous tissue within the articular capsule is a result of an ineffective anticoagulation process within an inflammed synovial joint. The subsequent lysis of the fibrinous tissue is also hindered following the formation of the fibrous tissue, whereat the synovial fluid becomes less viscous and elastic. Scars which may cause pain and ankylosis are formed whereat the fibrin is replaced by collagenous tissue following the invasion of mesenchymal cells such as fibroblasts.

In order to prevent the formation of scars, this invention introduces antithrombin (hereinafter referred to as AT) into the synovial fluid or other intracorporeal regions to inactivate thrombin necessary for fibrin formation.

AT is also mixed with a viscous material such as a sodium hyaluronate solution so that its effectiveness is prolonged as long as possible, wherein it can suppress the local coagulation system at the synovial cavity or other intracorporeal surgical regions.

Therefore, an administration method of AT has been invented for local use into the synovial cavity of patients with active arthritis.

This invention has an object of using as an injection at AT solution into the synovial cavity of the joint as therapeutic orthopaedics.

Furthermore, this AT solution can be administered locally to the internal region where any surgical operation beginning with the dissection of the skin is performed.

DETAILED DESCRIPTION OF THE PREFERRED EMBODIMENTS

For the purpose of improved treatment, this invention provides AT in a viscoelastic solution for therapeutic use. And this solution utilizes the characteristics of the elasto-viscous and protein binding effects of sodium hyaluronate solution, and a biological anti-coagulation effect of AT glycoprotein.

The biophysical element, AT, which inhibits thrombin action, theoretically exists in several types, such as, I, II, III, etc. However, only AT-III having a molecular weight between 58,000 and 65,000 has been proven to actually exist. Human AT is a glycoprotein of a molecular weight 58,000 made up of 425 amino acids in a single polypeptide chain crosslinked by three disulfide bridges. That is, it is synthesized in the liver, exists in the blood, and controls the coagulation system. It forms a complex with heparin and shows a strong anti-thrombin effect. AT-III gradually inhibits the action of thrombin when heparin is absent, and instantaneously neutralizes thrombin when heparin is present. In other words, heparin alone does not cause anti-coagulation, but it accelarates the action of AT-III.

Pharmacokinetic studies have shown AT to have a mean biological half-life of about 3.0 days in blood. The half-life is shortened in presence of heparin.

The quantity of AT in 1 ml normal pooled human plasma is conventionally taken as one unit (U). AT's potency assignment was determined from a standard calibrated against a World Health Organization (WHO) AT reference preparation. The concentration of AT in normal human plasma has been estimated at between 0.1 and 0.2 g/l, and thrombin inactivating activity levels are usually expressed either as a percentage of a reference plasma or as the IU number per ml of plasma, one IU per ml being equivalent to 100%.

In order to provide treatment for disseminated intravascular coagulation (D.I.C.) in the past, heparin was mainly administered therewith. However, it has already been shown that heparin does not work effectively when blood levels of AT have dropped. Accordingly, it has been recommended to administer dried concentrated human AT-III, so that the lack of AT can be corrected.

This invention is directed to the local administration of AT into the mammalian intracorporeal regions in order to improve the local hypercoagulability.

Ferbert et al., BWtPA Acute Embolic Apoplexy Investigation Group, U.S.A. and Germany, Medical Tribune, Japan, 1989, The 1st International Apoplexy Congress, recently studied the effectiveness of recombinant tissue plasminogen activator (t-PA) and reported that doctors should be cautious of postoperative hemorrhages resulting from the lysis of hemostatic thrombi, when using this strong fibrinolytic agent. On the other hand, AT inhibits fibrin formation and we should be cautious of inhibiting the wound healing process.

A solution having more than about 250 U/ml of AT should be avoided due to a higher tendency for spontaneous hemorrhaging.

The administration of an AT solution to patients having a hemorrhagic tendency or an inhibition to wound healing due to a deficiency of a blood coagulation factor, should be avoided.

HA, a large polysaccaride molecule, is present in nearly all connective tissue matrices of vertebrate organisms. In the human body, it is an important structural element in the skin, subcutaneous and interstitial connective tissues, synovial tissue and fluid, umbilical cord and the vitreous; its brief roles are speculated to be: (1) a vehicle for biophysical and biologically active elements; (2)adhesion to tissues and cells; (3)protection, separation and lubrication of tissues and/or cells; and (4)maintaining an equilibrium of water and sodium chloride within the connective tissues.

The molecular weight of a purified fraction of HA after isolation is known to be within the range of 50,000 to 13,000,000. It has been confirmed that the solution of deproteinized and purified sodium hyaluronate is safe for use in ocular surgery and osteoarthritis. The concentrations of sodium hyaluronate for ocular surgery and osteoarthritis are generally from 0.1 to 3% in weight. Its molecular weight generally ranges from about 500,000 to 5,000,000.

In view of the fact that the sodium hyaluronate solution needs at least three days to dissipate from the joint, this invention utilizes a mixture of AT with a viscous solution, whereas the AT works over an extended period to control the fibrin accumulation in the synovial cavity.

A physiological buffer solution mentioned in this specification includes distilled water with sodium chloride, buffers and/or stabilizers. Buffers are preferably selected from sodium phosphate and disodium phosphate, and stabilizers for AT are also preferably selected from sodium citrate, amino acetic acid, sodium glutamate, acetyltryptophan and sodium caprylate. These buffers and stabilizers are presently used for the sodium hyaluronate and AT solutions. The above mentioned buffers and/or stabilizers are favorable though this invention is not limited to any specific type of buffer or stabilizer, but rather to any usable solution which qualifies as a buffer/stabilizer.

The sterile final AT solution is used by either injection into the synovial cavity or by coating the tissue of the exposed internal surgical region intraoperatively.

The materials such as collagen type-IV, chondroitin sulfate (a molecular weight between 5,000 to 100,000), polyacrylamide (a molecular weight of about 1,000,000) and hydroxypropylmethylcellulose (a molecular weight of about 1,000,000) may be applicable as a substitute of the sodium hyaluronate or it may be combined with the sodium hyaluronate, even though, in this specification, HA is described as the preferred viscous substance due to its favorable elastoviscous and biophysical characteristics.

Artificially synthesized HA and AT would be applicable to the invented method of administration of an AT solution as a substitute of the previously mentioned variety of HA and AT-III compounds.

Without further elaboration, it is believed that one skilled in the art, using the preceding description, can utilize the present invention to its fullest extent. The following possible preferred administration examples for human are, therefore, to be construed as merely illustrative, and not limitative in any way whatsoever, for the remainder of the disclosure.

POSSIBLE METHOD OF ADMINISTRATION

Example I

Two tenths of a milliliter of the following AT solution are injected into the synovial cavity without removal of the synovial fluid from the joint.

Human AT-III having a molecular weight of about 59,000 is dissolved in a 1 ml physiological buffer solution to obtain a concentration of 50 U/ml.

POSSIBLE METHOD OF ADMINISTRATION

Example II

Two milliliters of the following AT solution are injected into the synovial cavity upon removal of 2 ml of the synovial fluid from the joint.

Ten units per milliliter of human AT-III having a molecular weight of about 58,000, and 100 mg of sodium hyaluronate having an average molecular weight of about 800,000, are dissolved in a 10 ml physiological buffer solution.

POSSIBLE METHOD OF ADMINISTRATION

Example III

Two milliliters of the following AT solution are injected into the synovial cavity without removing the synovial fluid from the joint.

Ten units per milliliter of human AT-III having a molecular weight of about 58,000, and 100 mg of sodium hyaluronate having an average molecular weight of about 800,000, are dissolved in a 10 ml physiological buffer solution.

POSSIBLE METHOD OF ADMINISTRATION

Example IV

The tissue of exposed and surgically traumatized abdominal organs is coated with the following AT solution during abdominal surgery, and the surgery is closed without removing the AT solution.

Ten units per milliliter of human AT-III having a molecular weight of about 58,000 and 1 g of sodium hyaluronate having an average molecular weight of about 4,000,000 are dissolved in a 100 ml physiological buffer solution.

POSSIBLE METHOD OF ADMINISTRATION

Example V

The tissue of exposed and surgically traumatized abdominal organs is coated with the following AT solution during abdominal surgery, and the surgery was closed without removing the AT solution.

Human AT-III having a molecular weight of about 58,000 is dissolved in a 100 ml physiological buffer solution to obtain a concentration of 50 U/ml. Simultaneously, 3 g of sodium hyaluronate having an average molecular weight of about 500,000 and 4 g of sodium chondroitin sulfate having an average molecular weight of about 25,000 are dissolved in the solution.

The preceding examples of possible method of administration can be repeated with similar success by substituting the generically or specifically described reactants and or operating conditions of this invention for those used in the preceding examples of possible method of administration.

By introducing this new method of administration of the AT solution into the synovial cavity of patients with active arthritis, fibrin formation in the synovial cavity can be prevented. In this regard, the invention decreases the complications seen with the excessive use of anti-arthritis drugs such as sodium aurothiomalate, penicillamine, antipyrine, aspirin, indomethacin and corticosteroids.

AT with a concentration from 0.5 to 250 U/ml and sodium hyaluronate having an average molecular weight between 350,000 and 8,000,000 with a concentration from 0.1 to 3% are recommended for effective treatment of the joint.

The average concentration of normal HA in the human synovial cavity is reported to be about 0.5 to 0.4% by Hadler et al. in 1979. A concentration as low as 0.1% HA solution is possible when the HA has a relatively high molecular weight, i.e. greater than 3,000,000, and a concentration as high as 1 to 3% is also possible when the HA has a relatively low molecular weight, i.e. lower than 1,000,000.

By introducing this invention not only to the joint but also to the intracorporeal surgeries (such as intraperitoneal, cesarean section, heart, lung, visceral, intracranial, ear, nose, throat and flexor tendon surgeries) postoperative pain, mechanical ileus, functional disturbance, motor disturbance or orthopaedic impairments due to scars caused by the fibrin clot formations in the surgical region can be prevented.

This invention is also useful for coating the exposed internal surgical region with the AT solution during the operation, and subsequently closing the surgery without removing the AT solution from the surgical region.

When using sodium hyaluronate of relatively low (as low as 50,000 to 1,000,000) or high (as high as 4,000,000 to 13,000,000) average molecular weight, the increased or decreased concentration of sodium hyaluronate would be possible in order to maintain an effective viscosity of the AT solution.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

We claim:

1. A surgical method, comprising the following steps:
   (a) performing intracorporeal surgery to a region of a mammal by dissecting the mammal's skin to expose tissue;
   (b) administering an antithrombin solution, including antithrombin at a concentration of more than 0.5 U/ml and not more than 250 U/ml and sodium hyaluronate having an average molecular weight between 50,000 and 13,000,000 with a weight concentration of at least 0.1% and not more than 3% dissolved in a physiological buffer solution, to the surgery region by coating the exposed tissue of the internal surgical region with the solution,
      wherein viscosity and elasticity of the solution is maintained through inhibition of fibrin formation with the antithrombin as fibrin binds to the sodium hyaluronate, thus inhibiting postoperative adhesion of the surgically traumatized organs; and
   (c) closing the surgery region without the removal of the antithrombin solution from the surgical region.

2. The method as claimed in claim 1, wherein step (a) comprises the step of performing surgery on a joint including synovial fluid.

3. The method as recited in claim 2, wherein step (b) further comprises replacing a portion of the synovial fluid of the joint with the antithrombin solution to maintain viscosity and elasticity of the synovial fluid after step (c).

4. The method as claimed in claim 2, wherein step (b) further comprises adding the antithrombin solution to the synovial fluid of the joint to maintain viscosity and elasticity of the synovial fluid after step (c).

5. A therapeutic method comprising the step of administering to mammals intrasynovially by injection an antithrombin solution to maintain viscosity and elasticity of synovial fluid by inhibiting fibrin formation with antithrombin as fibrin binds to sodium hyaluronate, whereby said solution includes antithrombin with a concentration of more than 0.5 U/ml and not more than 250 U/ml and sodium hyaluronate having an average molecular weight between 350,000 and 8,000,000 with a weight concentration of at least 0.1% and not more than 3%, which are dissolved in a physiological buffer solution.

6. The method of claim 5, further comprising the substep of adding sodium chondroitin sulfate to the antithrombin solution.

7. A surgical method for mammals, comprising the following steps;
   (a) performing intracorporeal surgery to a region by dissecting skin to expose tissue;
   (b) administering a solution, including antithrombin at a concentration of more than 0.5 U/ml and not more than 250 U/ml and a viscous substance which are dissolved in a physiological buffer solution, to the surgery region by coating the exposed tissue with the solution,
   wherein viscosity and elasticity of the solution is maintained through inhibition of fibrin formation with the antithrombin as fibrin binds to the viscous substance, thus inhibiting postoperative adhesion of the surgically traumatized organs; and
   (c) closing the surgery without removal of the solution from the surgical region.

8. The method as claimed in claim 7, wherein the viscous substance is selected from the group sodium chrondroitin sulfate, hydroxypropylmethylcellulose, polyacrylamide and collagen type-IV.

9. A surgical method for mammals, comprising the following steps;
   (a) performing intracorporeal surgery to a region by dissecting the skin to expose tissue;
   (b) adminstering a solution, including antithrombin at a concentration of more than 0.5 U/ml and not more than 250 U/ml which is dissolved in a physiological buffer solution, to the surgery region where a viscous substance is used,
   wherein viscosity and elasticity of the viscous substance is maintained by inhibiting fibrin formation with the antithrombin as fibrin binds to the viscous substance, thus inhibiting postoperative adhesion of the surgically traumatized organs; and
   (c) closing the surgery without removal of the antithrombin solution from the surgical region.

* * * * *

UNITED STATES PATENT AND TRADEMARK OFFICE
CERTIFICATE OF CORRECTION

PATENT NO. : 5,252,557
DATED : October 12, 1993
INVENTOR(S) : KITA et al.

It is certified that error appears in the above-indentified patent and that said Letters Patent is hereby corrected as shown below:

On the title page, item:

[56] At end of "OTHER PUBLICATIONS" insert:

--Ocular Surgery News, cover, pg. 40, vol. 9, No. 18, Sept. 15, 1991.

Arch Ophthalmol, pg. 1666, Vol. 108, December 1990.

Antithrombin, An Introduction, KabiVitrum, Sweden, June 1989.

Antithrombin III Kabi, Pamphlet, pgs. 57 & 58, KabiVitrum, Sweden.

Fragmin, Phamplet, pgs. 18, 19 & 40, Kami, Sweden 1988.

Healon, Pharmacia Ophthalmic, Inc., U.S.A.

Rosenberg, Actions and Interactions of Antithrombin and Heparin, New England Journal of Medicine, Jan. 16, 1975, pp. 146-151.

Ewa Marciniak et al., Catabolism and Distribution of Functionally Heterogeneous Human Antithrombin III, J. Lab. Clin. Med. January 1987, pp. 89-96.

Poster Symposium XVIII, Thrombosis: Structure and Activities of Antithrombin III, Thromb. Haemostas. 38:201A (1977), pp. 201-203.

Endre A. Balazs, chapter on Sodium Hyaluronate and Viscosurgery, Healon pp. 5-28.

UNITED STATES PATENT AND TRADEMARK OFFICE
CERTIFICATE OF CORRECTION

PATENT NO. : 5,252,557
DATED : October 12, 1993
INVENTOR(S) : KITA et al.

It is certified that error appears in the above-indentified patent and that said Letters Patent is hereby corrected as shown below:

Heparin, Lane and Lindahl, i Edward Arnold 1989, Great Britain, pp. Index 2-3, 18, 73-75, 164-165, 176, 180-181, 229-255, 260-262, 276-277, 288-291, 363-364, 366, 368, 388, 423, 438-439, 501, 562, 563-564, 577-578, 597-601.

Marciniak et al., Heparin-Induced Decrease in Circulating Antithrombin III, Lancet, Sept. 17, 1977, pp. 581-584.

Letters to the Editor of: Ocular Surgery News, Chicago, Ill, June 15, 1990, Page 3.

Joe Ho Kim, M.D., Intraocular Inflammation of Denatured Viscoelastic Substance In cases of Cataract Extraction and Lens Implantation, Journal of Cataract Refract, Surg.

Phillip C. Hoopes, Sodium Hyaluronate (HEALON®) in Anterior Segment Surgery: A Review and a New Use in Extracapsular Surgery Vol. 8, Spring 1982, pp. 184-159. AM Intra-Ocular Implant Society Journal.

Elizabeth D. Sharpe, M.D., A Prospective Comparison of AMVIScu and Healon® in Cataract Surgery, Vol. 12, January 1986, pp. 47-49.

Robert D. LeBoeuf et al., Human Fibrinogen Specifically Binds Hyaluronic Acid, The Journal of Biological Chemistry, Vol. 261, No. 27, pp. 12586-12592, 1986.

UNITED STATES PATENT AND TRADEMARK OFFICE
CERTIFICATE OF CORRECTION

PATENT NO. : 5,252,557
DATED : October 12, 1993
INVENTOR(S) : KITA et al.

It is certified that error appears in the above-indentified patent and that said Letters Patent is hereby corrected as shown below:

Bruce A. Barron et al., Comparison of the Effects of Viscoat and Healon on Postoperative Intraocular Pressure, American Journal of Ophthalmology 100:377-384, September, 1985.

Yoshitomi et al., Postoperative Fluctuations of Tissue Plasminogen Activator (t-PA) in Aqueous Humor Pseudophakes, pp. 1-9 w/Figs.

Proceedings of the Advanced Viscosurgery Techniques Symposium (1986), pp. 1-23. --

Col. 1, line 66, "though" should be --thought--.
Col. 6, line 5, "0.5" should be --0.15--.

Signed and Sealed this

Thirtieth Day of August, 1994

BRUCE LEHMAN

Attest:

Attesting Officer

Commissioner of Patents and Trademarks